United States Patent [19]

Dookhith et al.

[11] Patent Number: 5,206,021
[45] Date of Patent: Apr. 27, 1993

[54] STABILIZED OIL-IN-WATER EMULSIONS OR SUSPOEMULSIONS CONTAINING PESTICIDAL SUBSTANCES IN BOTH OIL AND WATER PHASES

[75] Inventors: Mohammad Dookhith, Raleigh, N.C.; Hubert Linares, Caluire, France

[73] Assignee: Rhone-Poulenc AG Company, Research Triangle Park, N.C.

[21] Appl. No.: 610,392

[22] Filed: Nov. 7, 1990

Related U.S. Application Data

[63] Continuation-in-part of Ser. No. 526,776, May 17, 1990, Pat. No. 5,096,711, which is a continuation of Ser. No. 343,043, Apr. 25, 1989, abandoned.

[30] Foreign Application Priority Data

May 9, 1988 [FR] France .................................. 88 06494

[51] Int. Cl.$^5$ ............................................. A01N 25/00
[52] U.S. Cl. ..................................... 424/405; 252/302; 252/313.1; 252/351; 252/352; 514/938
[58] Field of Search .................... 424/405; 514/938; 252/302, 313.1, 351, 352

[56] References Cited

U.S. PATENT DOCUMENTS

| | | | |
|---|---|---|---|
| 3,317,305 | 5/1967 | Stefik et al. | 71/3 |
| 3,873,689 | 3/1975 | Frensch et al. | 514/772.4 |
| 3,948,636 | 4/1976 | Marks | 71/112 |
| 4,188,202 | 2/1980 | Gillings et al. | 71/88 |
| 4,313,847 | 2/1982 | Chasin et al. | 252/356 |
| 4,372,943 | 2/1983 | Papanu et al. | 514/523 |
| 4,411,692 | 10/1983 | LeClair et al. | 71/93 |
| 4,594,096 | 6/1986 | Albrecht et al. | 71/93 |
| 4,678,503 | 7/1987 | Barlet et al. | 71/93 |
| 4,734,432 | 3/1988 | Szego et al. | 514/469 |
| 4,795,640 | 1/1989 | Helfenberger | 424/405 |
| 4,810,279 | 3/1989 | Martin | 71/121 |
| 4,818,536 | 4/1989 | Meyers et al. | 424/409 |
| 4,822,405 | 4/1989 | Martin et al. | 71/92 |
| 4,828,835 | 5/1989 | Meyers et al. | 424/409 |
| 4,853,026 | 8/1989 | Frisch et al. | 71/86 |

FOREIGN PATENT DOCUMENTS

| | | |
|---|---|---|
| 0070702 | 1/1983 | European Pat. Off. |
| 0289909 | 11/1988 | European Pat. Off. |
| 893391 | 1/1990 | Switzerland . |
| 2022418 | 12/1979 | United Kingdom . |
| 2082914 | 3/1982 | United Kingdom . |
| 2113116 | 8/1983 | United Kingdom . |

OTHER PUBLICATIONS

Schulman, J. H. and Leja J.; Kolloid-Z 136, 107–119 (1954); Control of Contact Angles At The Oil-Water-Solid Interfaces.

Scarlett, A. J., Morgan, W. L., & Hildebrand, J. H.; J. Phys. Chem. 31, 1556–71 (1927); Emulsification by Solid Powders.

Primary Examiner—Thurman K. Page
Assistant Examiner—Robert H. Harrison
Attorney, Agent, or Firm—James G. Passé

[57] ABSTRACT

The present invention relates to stabilized, concentrated or diluted emulsions of the oil-in-water (O/W) type exhibiting a pesticidal activity and to a process for making use of the emulsions. More specifically the invention relates to stable O/W macroemulsions which comprise one or more pesticidal active ingredients in the oil phase or additionally, macroemulsions which comprise one or more pesticidal active ingredients in both the oil and water phases, wherein the oily phase is emulsified or dispersed in the water phase by an emulsifying system; and wherein the emulsions are further stabilized by a solid dispersing agent, namely titanium dioxide, which maintains or improves the emulsion stability. It also relates to a suspoemulsion obtained by milling the said emulsion with an additional solid pesticidal substance.

15 Claims, No Drawings

STABILIZED OIL-IN-WATER EMULSIONS OR SUSPOEMULSIONS CONTAINING PESTICIDAL SUBSTANCES IN BOTH OIL AND WATER PHASES

This application is a continuation-in-part of copending application Ser. No. 07/526,776, filed May 17, 1990, U.S. Pat. No. 5,096,711, incorporated herein by reference, which is a continuation of application Ser. No. 07/343,043, filed Apr. 25, 1989, now abandoned.

BACKGROUND OF THE INVENTION

1. Field Of The Invention

The present invention relates to stabilized, concentrated or diluted emulsions of the oil-in-water (O/W) type exhibiting a pesticidal activity and to a process for making use of the emulsions. More specifically the invention relates to stable O/W macroemulsions which comprise one or more pesticidal active ingredients in the oil phase or additionally, macroemulsions which comprise one or more pesticidal active ingredients in both the oil and water phases, wherein the oily phase is emulsified or dispersed in the water phase by an emulsifying system; and wherein the emulsions are further stabilized by a solid dispersing agent, namely titanium dioxide, which maintains or improves the emulsion stability. It also relates to a suspoemulsion obtained by milling the said emulsion with an additional solid pesticidal substance.

2. Description Of Related Art

In general, an emulsion is the result of dispersing one immiscible liquid in another, and is made relatively stable by means of one or more emulsifying agents, which are usually surface-active agents.

The result is a "significantly stable" suspension of droplet particles of a certain size of a liquid homogeneously dispersed within a second immiscible liquid, defined as the continuous phase. The phase "significantly stable" is a relative one meaning relative to the intended use of the emulsion and to the relative ability of one emulsifying system vs. another to stabilize a given system of various differing components, which are additionally subject to various physical and chemical conditions or factors.

The basic factor in the stability or instability of an emulsion is the degree of interfacial tension (i.e., free energy) between the droplets of the dispersed liquid and the other continuous liquid phase. A high interfacial tension makes an emulsion inherently (basically) thermodynamically unstable.

The purpose of the emulsifying (or dispersing) agent, which is usually a surface-active agent, is to interact at the interface between the dispersed liquid droplets and the other continuous liquid phase. It thus functions to stabilize a basically unstable system by adsorption at the liquid/liquid interface as an oriented interfacial film. The result is a reduction in interfacial tension and a decrease in the rate of coalescence of the dispersed liquid particles by forming mechanical, steric and/or electrical barriers around them.

Emulsions may be categorized in two ways: first by the size of the dispersed particles (that is to say micro- vs. macroemulsions) and second by the nature of which phase forms the dispersed droplets and which is the continuous phase (that is to say oil-in-water O/W, vs. water-in-oil, W/O).

Both O/W and W/O micro- and macroemulsions are used for pesticidal compositions, the preference depending upon the system components and the required stability criteria. Macroemulsions generally have a dispersed droplet particle size from about 0.2 to about 50 microns. However, they are basically more unstable than a microemulsion (<0.2 microns), generally due to a wider particle size distribution whereby there is a higher tendency of larger droplets to coalesce with smaller ones and thus more readily break the emulsion.

The choice between O/W and W/O emulsions also depends upon the system components and the required stability criteria. An O/W is generally produced by emulsifying agents which are more soluble in the water than in the oil phase. The reverse generally provides W/O emulsions.

While the use of emulsions is frequently advantageous, their preparation and maintaining their stability frequently involves substantial experimentation (trial and error) and even when the compositions may have only limited stability in either their concentrated form or in end-use diluted compositions.

The emulsifying/dispersing system thus plays a key role in providing stable emulsions, but it is frequently complex and not easy to identify because of the required optimization of many different properties/characteristics such as the following:

There must be good surface activity to produce a low interfacial tension in the system used. The emulsifier must have the tendency to migrate to the interface rather than remain dissolved in either bulk phase.

The emulsifier must form, by itself or with other adsorbed molecules, a condensed lateral interfacial film.

The emulsifier must migrate to the interface at sufficient rate to reduce the interfacial tension to a low value during the time the emulsion is produced.

The emulsifier is best a mixture of a preferentially oil-soluble surface-active agent and a preferentially water-soluble one. This frequently produces a better and more stable emulsion.

An emulsifier that is preferentially water soluble (generally HLB of 8-18) will generally produce lower interfacial tension (i.e. contact angle <90°) at the water interface and produce O/W emulsions. Hydrophilic groups in the interfacial film provide a barrier to coalescence of oil droplets in O/W emulsions.

A suitable emulsifier for an O/W emulsion should give a PIT (phase inversion temperature) of 20°-60° C. higher than the normal storage temperature of the emulsion.

An emulsifier which inhibits or reduces components of the dispersed droplets from wetting the interfacial film (i.e., high contact angle between emulsifier in the film and the components in the droplet) will provide droplets that will not easily coalesce and thus stabilize the emulsion.

The above properties of a good emulsifying/dispersing system will thus determine the relative importance and influence of the following factors which are generally recognized by one skilled in the art to be important in determining emulsion stability (the resistance of emulsions to coalescence of their dispersed droplets—i.e., "resistance to breaking the emulsion").

The Physical Nature of Interfacial Film—mechanical strength and intermolecular forces.

The Existence of Electrical or Steric Barrier on the Droplets—significant in O/W emulsions.

The Viscosity of the Continuous Phase—reduced diffusion reduces droplet collision and thus reduces coalescense.

The Size Distribution of the Droplets—wider size distribution, especially in macroemulsions, allows larger droplets to coalesce at the expense of smaller droplets.

The Phase Volume Ratios—basic instability, especially in macroemulsions, tends to increase as the volume of the dispersed phase increases and the continuous phase decreases.

The Temperature—variation of temperature affects the nature and viscosity of the interfacial film/tension and can inverse or break the emulsion.

From the above discussion, it is thus readily obvious that even for one skilled in the art of emulsion technology, particularly in the area of pesticidal emulsions, the solutions frequently remain complex and each situation may encounter its own unique set of problems which are not necessarily limited to just the stability of the emulsion. Other factors or problems that must be considered include, for example:

Compositions containing more than one pesticidal substance, which differ significantly in chemical and physical properties, in particular where one is soluble in the lipophilic (oil) phase and the other is soluble in the water phase.

The need for improved overall safety characteristics of the composition, for example, by reducing/eliminating organic solvents which are frequently flammable, corrosive or toxic to living systems and are of environmental concern.

Instability resulting during ready to use aqueous dilution of initially stable concentrated emulsions.

For various reasons, including those aspects mentioned above, one may frequently prefer an O/W emulsion. Thus in the specific case of O/W emulsions for pesticidal use where the dispersed oily phase contains a lipophilic pesticidal substance, one or more solvents may be required in the case where the lipophilic substance is naturally in the solid state at the temperature or in the temperature region under consideration. On the other hand, the dispersing phase consists of water, optionally containing a water-soluble pesticidal substance, and a variety of other additives, specifically including surface-active agent(s) which are responsible for the interface between the two phases.

This basic outline, however, is far from enabling to a person skilled in the art to solve all the problems linked with the production of such emulsions in the case of each pesticide.

It is known, in fact, that preformed emulsions of pesticidal lipophilic substances in aqueous media tend to break when, as a result of a temperature variation, these substances change from the solid state into the liquid state, to return into the solid state (solidifying/melting).

This disadvantage is particularly detrimental when the melting points of such pesticidal substances are in the range of temperature variation within which the said substance is stored, because this makes the composition unsuitable for later use.

Similarly, it is known that in the case of pesticidal products which have a melting point below 100° C. it is very difficult to produce an aqueous suspension, because they begin to change state well before their melting point, and this consequently makes them difficult to mill. This is the case especially in hot countries, or in the summer in temperate regions.

These situations are further complicated when, in addition to the pesticidal substance in the oil phase, it is also desired that the composition contains another pesticidal substance soluble in the aqueous phase. This problem, in part, may result due to the tendency of the emulsion to break down because the water soluble pesticide may in itself behave as a surface-active agent, especially in the case of water soluble salts of these compounds. Their solubility in the aqueous phase then causes problems at the interfacial film between the oil and water phases. The result is that the dispersed oil droplet phase has an increased tendency to freely migrate/diffuse into the aqueous phase which leads to coalescence of the oil droplets and instability of the emulsion. Other aspects of the problem may include when is known as the salting out effect caused by high concentration of ions, especially inorganic ions, in the aqueous phase which causes the oil phase to separate out.

While it is known that O/W emulsions can be produced with some very specific systems where a pesticidal substance is only in the oil phase or optionally both the oil and water phases each contain a pesticidal substance, for example, as described in U.S. Pat. Nos. 4,810,279; 4,822,405; 3,873,689; 4,594,096; or in EP 70702 (apparently corresponding to U.S. Pat. No. 4,440,562), the technology is still unpredictable. This unpredictability may be seen, for example, in U.S. Pat. No. 4,853,026 which describes an initially formed O/W emulsion which surprisingly and rapidly inverts to W/O; GB 2,022,418A which only provides a W/O emulsion; EP 289,909A2, in which the examples demonstrate the critical nature and concentration of all the composition components—even slight changes outside the optimum concentrations produced a number of unstable O/W emulsions; or GB 2,082,914A which specifies that a very narrow size distribution is required for the dispersed oil droplet particles.

While the above emulsions, which unpredictably may or may not be stable, utilize well known and recognized ionic or non-ionic emulsifying/dispersing agents, which are surface-active agents, other persons have attempted by less known techniques to provide emulsification by solid powders. These may be present with or without other normal surface-active emulsifiers. Such powders may alternatively be referred to as dispersing or stabilizing agents. For example, unpredictably O/W or W/O emulsions are produced depending upon the interfacial contact angle provided by a specific powder, the nature of the oil and water components, the type of surface-active agents present, the nature of the surface of the powder, and the pH of the system, etc. Schulman et al., Kolloid-Z. 136, 107–119 (1954), reports emulsions stabilized by barium sulfate or co-precipitated barium sulfate-zinc sulfide powders. Scarlett et al., J. Phys. Chem., 31, 1566–1571 (1927) describes emulsification by a number of different powders including glass, copper, pyrite, zinc, charcoal and mercuric iodide. The type of emulsion produced, W/O or O/W, is highly variable and neither of these references describes compositions containing pesticidal substances.

In general, metals and metal oxides, including titanium dioxide, are known to be used in some types of pesticidal/agricultural formulations, for example as described in: DT 3004-010; DT 3005-016; DT 2804-141; J5 5020-750; J6 2004-210A; US 4,493,725; J5 8177-902A; J5 6086-105; or J5 6152-401. These compositions are, however, predominantly granular solids, powders, pastes or creams. In these applications, the function of the inorganic minerals, including that of titanium dioxide is typically as a pigment, a support or carrier, a controlled release agent, an anticaking agent, an antistatic agent, or an acid neutralizing agent.

Only in a few instances has titanium dioxide been disclosed for use in liquid pesticidal compositions, including emulsions. Here again, the purpose of titanium dioxide is usually as a pigment or a support. For example, U.S. Pat. No. 3,873,689, as mentioned previously discloses O/W emulsions. These emulsions contain inert white pigments, such as titanium dioxide, which are typically used at high concentration levels to provide a marking effect during spraying of end-use compositions.

While GB 213,116A does not describe emulsions for agrochemical/pesticidal uses, it does describe pharmaceutical, cosmetic or food emulsions which are W/O and which are stabilized by hydrophobic surface modified metals or metal oxides. The reference broadly discloses metal oxides including that of titanium, but only exemplifies silicas. The examples show that these hydrophobic surface modified suspending agents produce only W/O emulsions. However, on the other hand, while non-surface modified hydrophilic agents initially gave O/W emulsions, these were not stable and rapidly separated into three phases.

Furthermore, while EP 342,134So. Af. 89-3391, corresponding to copending U.S. Ser. No. 07/526,776, filed May 17, 1990 now U.S. Pat. No. 5,076,711 describes O/W emulsions which are stabilized by a titanium dioxide dispersing agent, these emulsions contain only a lipophilic soluble pesticidal substance. These emulsions don't contain any aqueous soluble pesticidal substances, which as discussed above, have a tendency to lead to unstable emulsions.

It is clearly obvious from the above that this emulsion technology is very complex, very specific and thus very unpredictable. Even extensive experimentation may not solve the numerous problems which exist and may not identify a simple uniform (widely applicable) solution to the problem(s), irrespective of the nature and concentration of the pesticidal substances, other adjuvants, processing conditions, and storage and application conditions of both concentrated and ready to use diluted O/W emulsions.

SUMMARY OF THE INVENTION

In its most general form, the invention relates to a stabilized pesticidal emulsion of the oil-in-water type (O/W), comprising:
 a. an oil phase containing a lipophilic pesticidal substance, optionally dissolved in an organic solvent;
 b. a water phase, optionally containing a compatible water-soluble pesticidal substance;
 c. an emulsifying system capable of emulsifying or dispersing the oily phase in the water phase; and
 d. a stabilizing or dispersing agent comprising titanium dioxide in an effective amount to further maintain or improve the stability of the emulsion.

More specifically the invention relates to stable O/W macroemulsions which comprise one or more pesticidal active ingredients in the oil phase or additionally, macroemulsions which comprise one or more pesticidal active ingredients in both the oil and water phases; and wherein said emulsions are further stabilized by a very fine solid dispersing agent, namely titanium dioxide. In particular, titanium dioxide is preferred to have a substantially hydrophilic surface and be of a uniformly fine particle size <1 microns, preferably between about 0.2–0.3 microns. It is further preferred that the size of the titanium dioxide particles be significantly smaller than the average diameter of the dispersed oil-phase droplets in the macroemulsion.

The invention also relates to a suspoemulsion obtained by milling the said emulsion with an additional solid pesticidal substance.

The invention also preferably relates to pesticidal O/W emulsions as described above comprising:
 a. an oil phase containing a lipophilic pesticidal substance which has a melting point below 100° C., optionally whereby the substance is dissolved in an organic solvent;
 b. a water phase, optionally containing a compatible water-soluble pesticidal substance;
 c. an emulsifying system capable of emulsifying or dispersing the oily phase in the water phase; and
 d. a stabilizing or dispersing agent comprising titanium dioxide in an effective amount to further maintain or improve the stability of the emulsion.

Furthermore, the invention also preferably relates to pesticidal O/W emulsions as described above comprising:
 a. an oil phase containing a lipophilic pesticidal substance which has a melting point situated within the range of temperature variation to which the said substance is subjected, during storage or preparation of the emulsion, optionally whereby the substance is dissolved in an organic solvent;
 b. a water phase, optionally containing a compatible water-soluble pesticidal substance;
 c. an emulsifying system capable of emulsifying or dispersing the oily phase in the water phase; and
 d. a stabilizing or dispersing agent comprising titanium dioxide in an effective amount to further maintain or improve the stability of the emulsion.

Generally the range of temperature variation described above is usually between about $-20°$ C. and about $+60°$ C.

Thus, an object of the present invention is to provide an oil-in-water (O/W) pesticidal emulsion exhibiting great stability.

A second object is to provide safer water based emulsion compositions by reducing or eliminating flammable and toxic organic solvents which may be detrimental to living species and to the environment.

A third object is to provide more easily prepared and convenient O/W pesticidal macroemulsions which, although having a wide particle size distribution which tends to give instability, are readily and easily stabilized against oil-phase droplet coalescence.

A further object is to provide O/W pesticidal macroemulsions which reduce or inhibit hydrolysis of hydrolytically unstable pesticidal substances, particularly esters, which are contained within the dispersed oil phase droplets.

A fifth object is to provide concentrated O/W pesticidal macroemulsions which are readily diluted with water for end-use application while maintaining good emulsion stability.

A sixth object is provide a stable pesticidal O/W macroemulsion which has additional or improved stabilization due to the presence of a very fine powdered stabilizing/dispersing agent which is insoluble in the system, highly inert, significantly reduces interfacial tension between the phases, and inhibits coalescence of oil-phase droplets.

A seventh object is to provide a stable O/W pesticidal macroemulsion which, besides having a pesticidal substance in the oil phase, additionally has dissolved in the aqueous phase a pesticidal substance, which may in the form of a salt thereof have a tendency to destabilize the emulsion.

Another object of the present invention is to stabilize an O/W emulsion containing a lipophilic pesticidal substance or a mixture of lipophilic pesticidal substances whose melting point is within the range of variation of preparation or storage temperature of the emulsion. More particularly, the present invention provides liquid, stable, improved compositions with lipophilic pesticidal products which have a melting point below 100° C.

These and other objects of the present invention shall become readily apparent from the detailed description of the present invention.

DETAILED DESCRIPTION OF THE INVENTION

The oil-in-water (O/W) emulsions, preferably macroemulsions with an average oil phase droplet size greater than about 1 micron, advantageously comprise, in grams/litre:

| | | | |
|---|---|---|---|
| a. | a lipophilic pesticidal substances(s) | 25 to 800 | |
| b. | a solvent | 0 to 350 | oily |
| c. | a hydrophobic surface-active emulsifying agent | 0 to 100 | phase |
| d. | a hydrophilic surface-active emulsifying agent | 20 to 60 | |
| e. | an optional compatible water soluble pesticidal substances(s) | 20 to 600 | |
| f. | a titanium dioxide-based dispersing or stabilizing agent and | 1 to 100 | |
| g. | water | balance to 1,000. | |

It has been found, quite unexpectedly, that the addition of small amounts of titanium dioxide, as a very fine solid/powdered dispersing agent, greatly improves the stability of oil-in-water emulsions.

Titanium dioxide is preferably present in a proportion of about 1 g/l to about 100 g/l of the emulsion, advantageously about 5 g/l to about 50 g/l, and preferably about 10 g/l to about 20 g/l in normal oil-in-water emulsions and about 10 g/l to about 30 g/l in suspoemulsions (suspended solid active ingredient in an oil-in-water emulsion of other active ingredients).

It is known that natural titanium dioxide crystallizes in three allotropic varieties: rutile, anatase and brookite, the former two being particularly preferred especially wherein they have a substantially hydrophilic surface. These three varieties are suitable within the scope of the present invention, wherein the form of titanium dioxide has an average particle size between about 0.1 and 1.0 microns, preferably between about 0.2 and about 0.3 microns. It is further preferred that the average particle size of titanium dioxide be significantly smaller (i.e., from about 2% to about 50%) in comparison to the average size of the dispersed oil droplets in the oil-in-water emulsions of the present invention.

Titanium oxide of the type described is available from the French company Thann et Mulhouse and in the United States from E. I. duPont de Nemours and Co. (Inc.).

The following are some of the characteristics or properties of titanium dioxide, functioning as a dispersing agent, which are believed to be responsible for the unexpectedly improved stability of the O/W pesticidal macroemulsions of the present invention.

1. Totally insoluble in both water and oil phases.
2. Migrates to and remains at the interface between the liquids and forms a coherent thin film around dispersed oil droplets, preventing the thinning of the liquid film between the dispersed droplets.
3. May be chemically/physically treated with surface modifiers to provide improved performance properties such as dispersibility in water. Provides ability to adsorb emulsifying agents and thus add to the stability of the interfacial film surrounding the dispersed droplets.
4. Neither to strongly hydrophilic nor too strongly hydrophobic, but preferably more hydrophilic, and thus not easily wetted by either oil or water phase.
5. Provides an appropriate finite contact angle at the liquid/liquid interface, preferably slightly less than 90°, which reduces the interfacial tension and favors an O/W emulsion.
6. Presents a barrier to contact of dispersed oil droplets, thus prevents/inhibits coalescence of the droplets and provides emulsion stability.
7. Very small average particle size (~0.1–1 micron, preferred 0.2–0.3 micron) in comparison to the average oil droplet particle size (~1–8 micron average).
8. Excellent chemical and physical stability. Retains very small particle size without clumping and maintains suspension. Flocculation/agglomeration of $TiO_2$ particles in fluid systems typically forms only loose clumps which are easily broken and redispersed under only moderate shear.
9. Low concentration, preferably 1–2%, in O/W concentrated emulsions, readily provides stable macroemulsions over broad temperature ranges and for extended time periods.
10. Further dilutions of the concentrated O/W emulsions with water for end-product use (e.g. in spray tank) continue to maintain emulsion stability.
11. Provides a protective film on dispersed oil droplets, containing active pesticidal ingredients, to prevent-/inhibit agglomeration or crystal growth of small particles into larger particles which may arise during temperature changes and/or freeze-thaw cycles of the emulsion on storage.
12. Is widely applicable/useable in numerous O/W emulsions generally irrespective of the nature of the pesticidal active component(s) which may be contained in the oil phase or contained in both the oil and in the water phase.

The pesticidal O/W emulsions, especially macroemulsions, of the invention, as described above, may be of the type where a) the pesticidal substance(s) is only in the oil phase or b) separate pesticidal substances are contained in each of the oil and water phases. A pesticide means either an active substance or a mixture, for example binary or ternary, of active substances. These pesticidal substances may exist as optical, geometric or stereoisomers, etc. Insecticides, fungicides, herbicides, plant growth regulators, nematicides, rodenticides and repellent products may be mentioned, no limitation being implied.

Regarding the lipophilic pesticidal substance referred to above, the melting point is preferably less than 100° C. and is generally in the range of storage temperatures which can usually vary between about −20° and about +30° C. Exceptional conditions may, of course, extend above or below the range defined above, but it should be understood that the formulations according to one of the preferred alternative forms of the invention can be used in all the cases where the temperature variation causes a change of state in the pesticide.

If these is a mixture of lipophilic substances, such a mixture may exhibit a eutectic point, well known in physical chemistry. Also, in the case of these mixtures, the invention will preferably relate to those whose eutectic point is below 100° C. or those whose eutectic point is situated within the temperature variation region, as defined above. Furthermore, however, the invention also relates to mixtures without a eutectic point, in which at least one of the substances corresponds to the above definition.

Lipophilic pesticidal substances are numerous and diverse and it is not part of the applicant's intention to limit the invention to any category of pesticidal whatever, except that, in the case of one of the preferred alternative forms of the invention, they must meet the criteria defined above, namely have a melting point below 100° C. or a melting point within the region of temperature variation as indicated above.

Among these lipophilic pesticidal substances with melting points below about 100° C., there may be mentioned phosalone, the aclonifenoxadiazon mixture, aclonifen-linuron, aclonifen-bifenox, bifenox, acephate, aclonifen, alachlor, aldicarb, amethryn, aminocarb, amitraz, azamethiphos, azinphos-ethyl, azinphos-methyl, aziprotryne, benolaxyl, benfluralin, bensulide, bensultap, benzoximate, benzoylprop-ethyl, bifenthrin, binopacryl, bromophos, bromo-propylate, bromoxynil esters, bupirimate, buthiobate, butocarboxim, carboxin, chlorbufam, chlordimeform, chlorfenson, chlormephos, chlorobenzilate, fluorochloridone, chloropropylate, chlorphoxim, chlorpropham, chlorpyrifos, chlorpyrifos-methyl, cloethocarb, cyanophos, cycloate, cycloxydim, cyfluthrin, demethon-S-methyl, desmetryn, dialifos, diazinon, diclofop, dicofol, diethatyl, dimethachlor, dimethomethryn, dimethoate, dinobuton, dinoseb, dioxabenzofos, DNOC (2-methyl-4,6-dinitrophenol), EPN (O-ethyl O-(4-nitrophenyl)-phenylphosphonothioate), etaconazole, ethalfluralin, ethiofencarb, ethofumesate, famphur, fenamiphos, fenitropan, fenobucarb, fenothiocarb, fenoxaprop, fenoxycarb, fenpropathrin, fenson, flanuprop, fluchloralin, fluorodifen, fluoroglycofen, flurecol, fluroxyupyr, formothion, furolaxyl, furmecyclox, haloxyfop, heptenophos, hymexazol, iodofenphos, ioxynil esters, isoprothiolane, linuron, metalaxyl, metazachlor, methamidophos, methidathion, methopotryne, metolcarb, monalide, monocrotophos, monolinuron, myclobutanil, napropamide, nitrapyrin, nitrofen, nitrothalisopropyl, oxabentrinil, oxadiazon, oxyfluorfen, parathion-methyl, penconazole, pendimethalin, pentanochlor, phenthoate, phosfolan, phosmet, piproctanil, pirimicarb, prochloraz, profluralin, promecarb, prometon, propachlor, propamocarb, propanil, propetamphos, propham, propoxur, propthoate, pyrazophos, pyridate, quinalphos, quizalofop, resmethrin, secbumeton, simetryn, tebutan, tefluthrin, temephos, tetramethrin, tetrasul, thiofanox, tolciofos-methyl, triadimefon, trichlorfon, tridiphane, triflumizole, trifluralin, and xylylcarb.

Other pesticides with melting points below 100° C. which can advantageously be used in the compositions of this invention include the various esters of the class of phenoxyalkanoic acids. These include for example:

2,4-D: (2,4-dichlorophenoxy) acetic acid esters;
2,4-DB: 4-(2,4-dichlorophenoxy) butyric acid esters;
2,4-DB: 2-(2,4-dichlorophenoxy) propionic acid esters and their optical isomers;
MCPA: (4-chloro-2-methylphenoxy) acetic acid esters;
MCPB: 4-(4-chloro-2-methylphenoxy) butyric acid esters; or
Mecoprop: 2-(4-chloro-2-methylphenoxy) propionic acid esters and their optical isomers.

The invention has been found to be particularly advantageous for those lipophilic pesticidal active ingredients which may be further subject to hydrolytic instability in their compositions during prolonged storage or on exposure to elevated temperatures. Amongst those compounds which may be mentioned are phenoxyalkanoic acid esters, other caroxylic acid esters, organophosphorous esters, and esters of phenols. In the latter case, the invention has been found to be particularly advantageous for bromoxynil esters, especially bromoxynil $C_1$–$C_8$ alkanoates by themselves or mixed, such as bromoxynil butanoate, heptanoate and octanoate, which are compounds that are well known in the art. The concentration of bromoxynil esters will advantageously vary between about 100 g/l and about 600 g/l, based on bromoxynil phenol, depending on the esters or ester mixtures employed.

If the lipophilic pesticidal substance requires it, which may be the case, it is dissolved in a suitable organic solvent. Within the scope of the present invention, the term solvent covers both a single solvent and a mixture of several solvents. The particular organic solvent is obviously not critical and any solvent or solvent mixture whatever may be employed which suitably dissolves the lipophilic pesticidal substance.

Among solvents there may be mentioned commercial solvents of aromatic/paraffinic nature, such as aromatic hydrocarbons sold under the trademark "SOLVESSO" or kerosenes, or solvents of an alkylaromatic, aliphatic or cycloaliphatic type, or else natural vegetable oils such as rape oil or modified oils. There may also be mentioned alcohols such as cyclohexanol, ketones such as cyclohexanone and aceto-phenone, chlorinated solvents such as carbon tetrachloride or chloroform, dimethylformamide and dimethyl sulphoxide.

It may be generally preferable to employ a pair of solvents, one being rather hydrophobic, such as the hydrocarbon solvents mentioned above, and the other being rather hydrophilic, such as the solvents containing functional groups referred to above. The balance between the hydrophobic solvent and the hydrophilic solvent is obviously a function of the nature of the pesticide or of the pesticide mixture.

For those pesticide substances which are compatible, water soluble and contained in the aqueous phase of the O/W emulsions of this invention, they may be soluble in their normally occurring form or as the result of base or acid addition salts thereof. By the term compatible, it is meant an agronomically acceptable pesticidal substance(s) which does not adversely interact physically or chemically with the other components of composition. These water soluble pesticidal substances or salts thereof may include, for example:

Acephate
Acifluorfen
Alloxydim
Amitrole
Ammonium sulphamate (AMS)
Arsenious acid Asulam
Benazolin
Bentazone
Benzsulfuron
Borax
Bordeaux mixture
Bromacil
Bromoxynil phenol
Carbendazim
Chloramben
Chlorfenac
Chlorimuron
Chlormequat
Chloroacetic acid
Chlorophonium
Chlorsulfuron
Clopyralid
2,4-D (2,4-dichlorophenoxy) acetic acid
2,4-DB 4-(2,4-dichlorophenoxy) butyric acid
2,4-DES 2-(2,4-dichlorophenoxy)ethyl hydrogen sulphate
Dalapon
Daminozide
Demeton-S-methylsulphon
Dicamba
Dichlorophen
Dichlorprop (2,4-DP)
Dicrotophos
Difenzoquat
Dikegulac
Dimethirimol
Dimethylarsinic acid
4,6-Dinitro-o-cresol (DNOC)
Dinoseb
Dinoterb
Diquat
Dodine
Enothal
Etacelasil
Etaphon
Fenaminosulf
Fenoprop
Fluoroacetamide
Fomesafen
Formaldehyde
Formetanate
Fosamine
Fosetyl
Glufosinate
Glyphosate
Guazatine
Hexazinone
2-Hydrazinoethanol
Hydrogen cyanide
Imazapyr
Imazaquin
Imazethapyn
Imazilil
Indol-3-ylacetic acid
4-Indol-3-ylbutyric acid
Ioxynil phenol
Maleic hydrazide
MCPA (4-chloro-o-tolyloxy)acetic acid
MCPB 4-(4-chloro-o-tolyloxy)butyric acid
Mecoprop
Mefluidide
Mepiquat
Mercuric chloride
Metham
Methamidophos
Methomyl
Methylarsenic acid
Metsulfuron
Mevinphos
Monocrotophos
Nabam
Naptalam
2-(1-Naphthyl)acetic acid
(2-Naphthyloxy)acetic acid
Nicosulfuron
Omethoate
Oxamyl
Oxydemeton-methyl
Paraquat
Pentachlorophenol
Perfluidone
2-Phenylphenol
Phosphamidon
Picloram
Piproctanyl
Primsulfuron
Propamocarb
Sethoxydim
Sodium chlorate
Sodium fluoride
Sodium fluoroacetate
Sulfometuron
2,4.5-T (2,4,5-trichlorophenoxy)acetic acid
2.3.6-TBA (2,3,6-trichlorobenzoic acid)
TCA (trichloroacetate)
TEPP (ethyl pyrophosphate)
Thiameturon
Thiocyclam
Triasulfuron
Trichlorfon
Triclopyr
Validamycin
Vamidothion.

Within the above general type of compounds, or those specifically named, there are compounds with melting points greater than 100° C. such as sulfonyl ureas or imidazolyl compounds. These compounds may additionally comprise the lipophilic soluble substance within the broadest definitions of this invention.

Among the surfactants, particular mention is made of nonionic surfactants which are the result of reaction of at least one mole of alkylene oxide, especially propylene oxide or ethylene oxide, with an organic compound containing at least six carbon atoms and one active hydrogen atom. These organic compounds include phenols and aliphatic alcohols, mercapto compounds such as dodecyl mercaptan, oleyl mercaptan and cetyl mercaptan, thiophenols and thionaphthols, carboxylic acid amides, sulphonamides, and compounds which are block co-polymer of ethylene oxide and propylene oxide, sold under the trademark "PLURONIC", as described in U.S. Pat. No. 2,674,619.

It is generally desirable to employ products containing at most 30 moles of alkylene oxide (especially ethylene oxide) per residue of the above mentioned organic compound.

Among the surfactants referred to above, preference is given to:

The products of addition of ethylene oxide to an alkylphenol: The alkylphenols contain one or more alkyl radicals attached to the phenol nucleus, the total number of carbon atoms in the alkyl chain(s) ranging from 7 to 24, the preferred alkylphenols being those which contain 1 or 2 alkyl groups, each containing 7 to 12 carbon atoms. These alkylphenols also include the methylenephenols obtained, for example, by condensing phenols with formaldehyde. A particularly advantageous example is the product of condensation of 1 to 20 ethylene oxide unit with nonylphenol;

The products of addition of ethylene oxide to a condensation product obtained by attaching compounds containing phenolic hydroxyl groups to compounds containing olefinic double bonds and carbon rings: The following may be mentioned as representing such condensation products: mono(1-phenylethyl)phenol, di(1-phenylethyl)phenol, tri(1-phenylethyl)phenol, diphenylisopropyl phenol, mono(1-phenylethyl)cresol, (1-phenylethyl)naphthol and dicyclohexylphenol. It will be noted that the 1-phenylethyl functional group is commonly called the styryl functional group. The condensation products may be subjected to the alkoxylation in the form of single bodies, but it is also possible to employ them in the form of mixtures, such as are commonly obtained in the addition by linking. Among these, preference is given to mono-, di- or tri(1-phenylethyl)phenols or, more commonly called, styrylphenols.

All these surfactants are well known to a person skilled in the art. By way of example, reference can usually be made to French Patent No. 1,395,059, granted on Mar. 1, 1965, no limitation being implied.

Nevertheless, within the scope of the present invention, it is preferred to choose an emulsifying system made up of two nonionic surface-active agents, one having hydrophilic properties and the other lipophilic or hydrophobic properties. Particularly preferred amongst the hydrophobic surfactants are those which have a low HLB (hydrophiliclipophilic-balance) and can act to prevent or inhibit crystal growth of a lipophilic active ingredient. This is best achieved when the hydrophobic surfactant mixes with and/or solubilizes in the active ingredient to significantly lower the melting point thereof. Especially advantageous for this use are the hydrophobic ethoxylated nonylphenol surfactants described above.

Thus, among the surface-active agents referred to above there are chosen, in the case of the hydrophilic agents, those which contain at least 7 alkylene oxide units; whereas surface-active agents containing fewer than 7 alkylene oxide units are chosen in the case of lipophilic surface-active agents.

In addition to this basic composition, it is advantageous to incorporate an anionic surfactant like sulphonic acids, such as long-chain alkylbenzene-sulphonates, optionally in the form of amine or ammonium salts. For example, ammonium dodecylbenzenesulphonate is advantageously employed. With reference to the composition described above, between about 0 and 10 g/liter, preferably about 2 to 10 g/liter of the anionic surfactant is employed.

In order to lower the solidification point of the emulsion and, consequently, to promote the pourability of the composition, it is also possible to incorporate one or more plasticizing diols such as ethylene glycol, propylene glycol, glycerol, di- or tri- or tetraethylene glycol, in a quantity which usually varies between about 0 and 50 g/l, with reference to the composition defined above.

It is also possible to incorporate in the compositions according to the invention all kinds of other ingredients and especially antifoam agents such as a silicone oil (silicone oil-silica mixture), certain alcohols or phenols which have few ethoxy units, biocidal agents such as citric, propionic and benzoic acids, or their salts or esters, in a quantity which usually varies between about 0 and 50 g/l with reference to the composition defined above.

In addition to the above mentioned constituents, the compositions according to the invention may contain up to about 50 g/l of thickeners. Thickeners are products which, when added to the emulsions according to the invention, impart pseudoplasticity properties to them. The thickeners which may be employed in the invention may be inorganic and/or organic in nature. As a thickener of an inorganic type there may be mentioned attapulgites, bentonites, caponites and colloidal silicas. As a thickener of an organic type there may be mentioned hydrophilic biopolymers of the heteropolysaccharide type of a thickening character, water-soluble polymers such as celluloses, methyl cellulose and acrylic derivatives, and vinylpyrrolidone.

The hydrophilic biopolymers of the heteropolysaccharide type which may be employed in the invention are known products. They have a molecular weight higher than 200,000 and preferably higher than 1,000,000; they have pseudoplasticity properties and are generally obtained by the action (i.e. by fermentation) of bacteria of the genus Xanthomonas on carbohydrates. These biopolymers are also sometimes referred to by a variety of other expressions such as: Xanthomonas hydrophilic colloids, heteropolysaccharide resins, xanthan resins, extracellular heteropolysaccharides originating from Xanthomonas or from bacteria of the Pseudomonadaceae family. The word biopolymer is employed to mean that a polymer originating from a biological process (bacterial fermentation in this case) is involved.

The bacteria employed for the preparation of these biopolymers are in most cases *Xanthomonas campestris*, but it is also possible to employ other Xanthomonas such as *Xanthomonas carotae, Xanthomonas incanae, Xanthomonas begoniae, Xanthomonas malvacearum, Xanthomonas vesicatoria, Xanthomonas traslucens* or *Xanthomonas vasculorum*. Suitable carbohydrates for fermentation with the aid of suitable carbons for the fermentation, with the aid of Xanthomonas bacteria are glucose, sucrose, fructose, maltose, lactose, galactose, starch, potato starch, etc.

Other adjuvants which may also be employed with the emulsions of this invention are penetrating, wetting, or translocating promoting agents. Such agents may additionally have properties referred to as bioactivation. Examples of these are: ethoxylated tallow amine; ethoxylated diamine; glycerine; sorbitol; polyethylene glycol; ammonium sulfate; linear alcohol ethoxylate; nonylphenol ethoxylate; dioctyl sulfosuccinate; alcohol ether sulfates; and organosilicone surfactants, such as polyalkylene oxide modified dimethyl polysiloxane copolymers sold under the trademark "SILWET" L-77.

The above oil-in-water concentrated emulsions may be prepared by any convenient method, but are preferably prepared by a) the combination of the hydrophobic nonionic surface-active agent with a mixture of the lipophilic pesticide and solvent as required and then b) the combination of the resulting lipophilic mixture with the aqueous phase containing the hydrophilic surfactant, the dispersing agent and the optional water soluble pesticide. This last stage is accompanied by stirring to form the emulsion. An emulsion of more mediocre quality is obtained when the nonionic surface-active agent(s) (emulsifiers) are added to the aqueous phase in the emulsion-forming step.

The addition may also be performed using a reverse method. This means placing the oily phase in the aqueous phase and this is an additional advantage of titanium dioxide. The emulsion obtained is next homogenized by various methods to form a macroemulsion.

One method of homogenization consists of employing an efficient disperser or a bead mill or a colloid mill or an Apu Gaulin-type plunger homogenizer to obtain a macroemulsion with a droplet size of appropriate diameter (average diameter in the range of about 1–8 microns and an overall size distribution in the range of about 1–15 microns).

The pesticidal emulsions according to the invention are used by dilution with water so as to obtain an effective pesticidal composition. For example, all of these emulsions can be applied for the control of pests, as stable O/W emulsified spray mixtures, etc., whereby the concentrated emulsion is diluted from about 10 to about 200 fold with water. For application to crops for example, a final spray mixture may be generally applied at a rate in the range of about 100 to about 1200 liters per hectare, but may be higher or lower (e.g. low or ultra-low volume) depending upon the need or application technique.

As already briefly mentioned in the preamble of the description, emulsions such as just described can lead to excellent suspoemulsions by addition of a solid pesticidal substance which is then milled by means of a mill. These suspoemulsions are especially useful in the case of mixtures with carbaryl or thiodicarb.

The examples below illustrate the invention:

EXAMPLE 1

A homogeneous oily mixture was obtained by mixing in a container with stirring, phosalone (350 g), acetophenone (200 g), a $C_{10}$–$C_{13}$ aromatic solvent sold under the trademark "SOLVESSO" 200 (50 g), and a nonylphenol ethylene oxide polycondensate (1 EO; 50 g).

Similarly, by mixing in another container, with stirring and while heating to about 40° C., water (390 cc), an ethylene oxide/propylene oxide condensate (EO:PO 70:30; 40 g), melted beforehand, a dodecylbenzenesulphonate amine salt (4 g), propylene glycol (20 g), attapulgite (12 g), titanium dioxide in anatase form (12 g), and antifoam (2 g), a homogeneous aqueous dispersion was obtained.

The oily mixture was then run into the aqueous mixture in a well-stirred vessel and was made up to 1 litre by adding water if necessary. This mixture was then homogenized by being passed through a bead mill (1-mm glass beads).

The emulsion obtained has the following composition (in g/l):

| | | |
|---|---|---|
| phosalone, 6-chloro-3-diethoxyphosphino-thioylthiomethyl-1,3-benzoxazol-2(3H)-one | 350 | |
| acetophenone | 200 | oily phase |
| SOLVESSO ® 200 $C_{10}$–$C_{13}$ aromatics | 50 | |
| 1:1 ethylene oxide/nonylphenol condensate | 50 | |
| propylene oxide/ethylene oxide condensate (EO:PO 70:30) | 40 | |
| dodecylbenzenesulphonic acid amine salt | 4 | |
| propylene glycol | 20 | |
| attapulgite | 12 | |
| titanium dioxide in anatase form | 12 | |
| antifoam | 2 | |
| balance water up to 1 liter | | |

The following examples were produced using the same method.

EXAMPLE 2

The following emulsion was produced (in g/l):

| | | |
|---|---|---|
| oxadiazon, 5-t-butyl-3-(2,4-dichloro-5-isopropoxyphenyl)-1,3,4-oxadiazol-2(3H)-one | 100 | |
| aclonifen, 2-chloro-6-nitro-3-phenoxy-benzenamine | 300 | oily phase |
| acetophenone | 300 | |
| 1:1 ethylene oxide/nonylphenol condensate (1 EO) | 50 | |
| propylene oxide/ethylene oxide condensate (EO:PO 70:30) | 34 | |
| dodecylbenzenesulphonic acid amine salt | 3.4 | |
| propylene glycol | 17 | |
| attapulgite | 10 | |
| titanium dioxide in anatase form | 10 | |
| antifoam | 1.7 | |
| balance water up to 1 liter | | |

EXAMPLE 3

The following emulsion was produced (in g/l):

| | | |
|---|---|---|
| linuron, N'-(3,4-dichlorophenyl)-N-methoxy-N-methylurea | 83 | |
| aclonifen, 2-chloro-6-nitro-3-phenoxy-benzenamine | 250 | oily phase |
| acetophenone | 350 | |
| 1:1 ethylene oxide/nonylphenol condensate (1 EO) | 20 | |
| propylene oxide/ethlene oxide condensate (EO:PO 70:30) | 35 | |
| dodecylbenzesulphonic acid amine salt | 3.5 | |
| propylene glycol | 19 | |
| attapulgite | 10 | |
| titanium dioxide in anatase form | 10 | |
| antifoam | 2 | |
| balance water up to 1 liter | | |

EXAMPLE 4

The following emulsion was produced (in g/l):

| | | |
|---|---|---|
| bifenox, methyl 5-(2,4-dichlorophenoxy)-2-nitrobenzoate | 105 | |
| aclonifen, 2-chloro-6-nitro-3-phenoxy-benzenamine | 311 | oily phase |
| acetophenone | 330 | |
| 1:1 ethylene oxide/nonylphenol condensate (1 EO) | 50 | |
| propylene oxide/ethlyene oxide condensate (EO:PO 70:30) | 35 | |
| dodecylbenzenesulphonic acid amine salt | 4 | |
| propylene glycol | 20 | |
| attapulgite | 12 | |
| titanium dioxide in anatase form | 12 | |
| antifoam | 2 | |
| balance water up to 1 liter | | |

EXAMPLE 5

| | | |
|---|---|---|
| phosalone, 6-chloro-3-diethoxyphosphino-thioylthiomethyl-1,3-benzoxazol-2(3H)-one | 450 | oily phase |
| acetophenone | 200 | |
| SOLVESSO 200, $C_{10}$–$C_{13}$ aromatics | 100 | |

| | |
|---|---|
| -continued | |
| propylene oxide/ethylene oxide condensate (EO:PO 70:30) | 34 |
| dodecylbenzenesulphonic acid amine salt | 3 |
| propylene glycol | 17 |
| attapulgite | 10 |
| titanium dioxide in anatase form | 10 |
| antifoam | 2 |
| balance water up to 1 liter | |

EXAMPLE 6

The following emulsion was produced (in g/l):

| | | |
|---|---|---|
| alachlor, α-chloro-2',6'-diethyl-N-methoxymethylacetanilide | 180 | ⎫ |
| aclonifen, 2-chloro-6-nitro-3-phenoxy-benzenamine | 210 | ⎬ oily phase |
| acetophenone | 200 | |
| SOLVESSO ® 200, $C_{10}$–$C_{13}$ aromatics | 50 | |
| 2:1 ethylene oxide/nonylphenol condensate | 50 | ⎭ |
| propylene oxide/ethylene oxide condensate (EO:PO 70:30) | 34 | |
| dodecylbenzenesulphonic acid amine salt | 4 | |
| propylene glycol | 20 | |
| attapulgite | 12 | |
| titanium dioxide in rutile form | 12 | |
| antifoam | 2 | |
| balance water up to 1 liter | | |

EXAMPLE 7

The following emulsion was produced (in g/l):

| | | |
|---|---|---|
| alachlor, α-chloro-2',6'-diethyl-N-methoxymethylacetanilide | 143 | ⎫ |
| aclonifen, 2-chloro-6-nitro-3-phenoxy-benzenamine | 257 | ⎬ oily phase |
| acetophenone | 150 | |
| SOLVESSO ®, $C_{10}$–$C_{13}$ aromatics | 50 | ⎭ |
| propylene oxide/ethylene oxide condensate (EO:PO 70:30) | 47 | |
| dodecylbenzenesulphonic acid amine salt | 4.7 | |
| propylene glycol | 24 | |
| attapulgite | 14 | |
| titanium dioxide in anatase form | 14 | |
| antifoam | 2.4 | |
| hydroxypropyl cellulose | 1 | |
| balance water up to 1 liter | | |

EXAMPLE 8

| | | |
|---|---|---|
| ethoprofos, O-ethyl-S,S-dipropylphosphorodithioate | 400 | ⎫ oily phase |
| acetophenone | 50 | ⎭ |
| propylene oxide/ethylene oxide condensate (EO:PO 70:30) | 60 | |
| dodecylbenzenesulphonic acid amine salt | 6 | |
| propylene glycol | 30 | |
| attapulgite | 17 | |
| titanium dioxide in rutile form | 17 | |
| antifoam | 3 | |
| colorant | 0.1 | |
| balance water up to 1 liter | | |

EXAMPLE 9

The following emulsion was produced (in g/l), with bromoxynil ester amounts based upon bromoxynil phenol:

| | | |
|---|---|---|
| bromoxynil octanoate, 94%, 2,6-dibromo-4-cyanophenyl octanoate | 112.5 | ⎫ |
| bromoxynil heptanoate, 94%, 2,6-dibromo-4-cyanophenyl heptanoate | 112.5 | ⎬ oily phase |
| SOLVESSO ® 200, $C_{10}$–$C_{13}$ aromatics | 100 | ⎭ |
| propylene oxide/ethylene oxide condensate (EO:PO 70:30) | 60 | |
| dodecylbenzenesulphonic acid amine salt | 6 | |
| propylene glycol | 30 | |
| attapulgite | 20 | |
| titanium dioxide in anatase form | 20 | |
| hydroxypropyl cellulose | 2 | |
| balance water up to 1 liter | | |

EXAMPLE 10

The following emulsion was produced (in g/l), with bromoxynil ester amounts based upon bromoxynil phenol:

| | | |
|---|---|---|
| bromoxynil octanoate, 94%, 2,6-dibromo-4-cyanophenyl octanoate | 112.5 | ⎫ |
| bromoxynil heptanoate, 94%, 2,6-dibromo-4-cyanopheynyl heptanoate | 112.5 | ⎬ oily phase |
| esterified rape oil | 50 | ⎭ |
| propylene oxide/ethylene oxide condensate (EO:PO 70:30) | 60 | |
| dodecylbenzenesulphonic acid amine salt | 6 | |
| propylene glycol | 30 | |
| attapulgite | 20 | |
| titanium dioxide in anatase form | 20 | |
| hydroxypropyl cellulose | 2 | |
| balance water up to 1 liter | | |

EXAMPLE 11

The following suspoemulsion (suspended thiodicarb) was produced (in g/l): technical thiodicarb, N,N'-[thiobis[(methylimino)carbonyloxy]]bis[ethanimidothioate], (92%, 163 g) is dispersed with stirring in a mixture containing:

| | |
|---|---|
| 7:1 ethylene oxide/polyarylphenol sulphate condensate (7 EO) | 25 |
| complex phosphoric ester | 25 |
| ethylene oxide/nonylphenol polycondensate with 2, 7 and 10 EO (1:1:1) | 80 |
| deodorizer, salicylate | 10 |
| attapulgite | 20 |
| titanium dioxide in anatase form | 20 |
| antifoam | 5 |
| balance water up to 1 liter | |

A dispersion of solid in water was therefore obtained. For the oil phase, technical ethion, S,S'-methylenebis-(O,O-diethyl phosphorodithioate), (96%, 391 g) was then added and a homogeneous suspoemulsion, was obtained, which was milled in a bead mill.

EXAMPLE 12

The following suspoemulsion (suspended carbaryl) was produced (in g/l) under the same conditions as above:

| | | |
|---|---|---|
| technical ethion, 96%, S,S'-methylenebis-(O,O-diethylphosphorodithioate) | 261 | ⎫ oily phase |
| technical carbaryl, 92%, 1-naphthalenyl methylcarbamate | 229 | ⎭ |
| 7:1 ethylene oxide/polyarylphenol sulphate polycondensate (7 EO) | 50 | |
| ethylene oxide/nonylphenol polycondensate | 85 | |

-continued

| with 2, 7 and 10 EO (1:1:1) | |
|---|---|
| deodorizer, salicylate | 10 |
| attapulgite | 15 |
| titanium dioxide in anatase form | 30 |
| balance water up to 1 liter | |

The dispersed oil droplet particle size determined in some of the selected examples above was as follows:

| Example No. | Average Size, microns | 90% < Size, microns |
|---|---|---|
| 1 | 2 | 4 |
| 2 | 1 | 2 |
| 3 | 1.5 | 3 |
| 5 | 4 | 9 |
| 6 | 1 | 2 |
| 11 | 5 | 13 |
| 12 | 4 | 12 |

EXAMPLE 13

Stability Test

The compositions were then subjected to various stability tests:
First, these compositions were subjected to five cycles of uniform temperature variations during five weeks from −10° C. to 35° C.
Second, these compositions were placed for one month in an oven at 50° C.
Third, these compositions were placed at 35° C. for three months.
It was found that these compositions exhibit no phase separation or flocculation phenomena at the end of these three tests.

Comparative Test

By way of a comparative example, an emulsion was produced according to Example 2, but leaving out titanium dioxide.

On being treated as shown above for 1 month at 50° C., this emulsion separated into two phases which were not reversible by stirring, making it unsuitable for use.

The following EXAMPLES 14–20 of titanium oxide stabilized oil-in-water macroemulsions, specifically as herbicidal combinations, were prepared containing several pesticidal active ingredients to exemplify a further aspect of the invention wherein the oil phase contains one or more lipophilic active ingredients and the aqueous phase contains one or more water soluble (hydrophilic) active ingredients. These concentrate compositions, as well as others described within the scope of this invention, can be readily diluted with water to give stable sprayable compositions at concentrations suitable for use in field applications as previously described. The components/ingredients which were used in these formulations are listed below by their generic chemical descriptions.

| Common/Trade Name/Mark | Chemical Description |
|---|---|
| A. Active Ingredients, A.I. | |
| Glyphosate IPA | N-(phosphonomethyl)glycine isopropylamine salt |
| 2,4-D TIPA, 75% | (2,4-dichlorophenoxy)acetic acid tris(2-hydroxypropyl)amine salt |
| 2,4-D IOE, 90% | (2,4-dichlorophenoxy)acetic acid isooctyl ester |
| 2,4-DP IOE, 90% | (2,4-dichlorophenoxy)propionic acid isooctyl ester |
| 2,4-D DMA, 75% | (2,4-dichlorophenoxy)acetic acid dimethylamine salt |
| Bromoxynil octanoate, 92% | 2,6-dibromo-4-cyanophenyl octanoate |
| Bromoxynil heptanoate, 93% | 2,6-dibromo-4-cyanophenyl heptanoate |
| B. Adjuvants | |
| "TENNECO" ® 200 | $C_{10}$–$C_{13}$ aromatic hydrocarbons, solvent |
| TENECCO 500/100 | mixed xylenes and $C_9$ + solvent naphtha, solvent |
| "SILWET" ® L-77 | polyalkylene oxide modified silanes, bioactivator |
| "SOPROMINE" ® S30 | ethoxylated (20 EO) tallow amine, wetting/penetrating agent |
| Propylene glycol | 1,2-propanediol, antifreeze agent |
| "ATLAS" ® G3300 | dodecylbenzensulfonic acid amine salt, anionic dispersing/emulsifying agent |
| "GERONOL" ® 724P | ethylene oxide/propylene oxide block co-polymer (EO:PO 70:30), emulsifier |
| "SAG" ® 30 | silicone, antifoam |
| "ATTAGEL" ® 50 | attapulgite clay, thickener/diluent |
| "METHOCEL" ® E50LV | hydroxypropyl methyl cellulose, thickener |
| "CARBOPOL" ® 910 | acrylic acid polymer, thickener |
| "BIOZAN" | xanthan gum, thickener |
| "TI-PURE" ® | titanium dioxide, rutile form of 0.2–0.3 micron particle size, dispersing/stabilizing agent. |

The general procedure used for the preparation of these concentrated compositions utilized the actual technical active ingredient or as is adjuvant weights in g/l and was as follows:

a. A homogeneous oil-phase was prepared by thoroughly mixing the oil-phase active ingredient(s) and optionally, if necessary, a solvent, e.g. "TENNECO"(trademark) 200 or also optionally, if necessary, a hydrophobic surface active agent.

b. A homogenous water-phase was prepared by thoroughly mixing the water-phase active ingredient(s) and adjuvants: e.g., propylene glycol (antifreeze/pourability agent); "GERONOL"(trademark) 724P (emulsifier, previously melted at 50° C.); "ATLAS"(trademark) G3300 (dispersing/emulsifying agent); Glyphosate IPA (technical active ingredient as a 62% aqueous solution); 2,4-D TIPA (technical active ingredient as an aqueous solution); "SOPROMINE"(trademark) S30 (wetting and penetrating agent); "SAG"(trademark) 30 (antifoam agent); water (carrier); $TiO_2$ (stabilizing/dispersing agent); and "ATTAGEL"(trademark) 50 (clay diluent/- thickener). While these ingredients were preferably added in this sequence, the order can generally be that which is convenient and maintains the water-phase homogeneity; in this regard, the propylene glycol is best added before the "GERONOL" (trademark) 724P. As required, the pH of the aqueous phase may be adjusted now or after mixing in part c). A preferred pH is generally in the range of about 4 to about 7-8 and is obtained by addition of about 0.1N NaOH or HCl.

c. The oil-phase was gradually added to the well stirred water-phase and made up to one liter by adding water if necessary. The addition may also be performed in a reverse method. This mixture was then homogenized by passing it through a homogenizing mixer, e.g., a bead mill with 1-1.5 mm Zicor beads. These final oil-in-water emulsions were determined to have an average particle size of the dispersed oil droplets of about 2-8 microns; more preferably 3-5 microns; an overall size distribution was in the range of 1-15 microns. Good to excellent stability of these emulsions was confirmed in extended time and high temperature studies similar to those described above.

EXAMPLE 14

The following emulsion was produced (in g/l):

| | | |
|---|---|---|
| 2,4-D IOE | 176 | } oily phase |
| 2,4-D TIPA | 299 | |
| Glyphosate IPA | 182 | |
| SOPROMINE (trademark) S30 | 100 | |
| Propylene glycol | 30 | |
| ATLAS (trademark) G3300 | 5 | |
| GERONOL (trademark) 724P | 40 | |
| SAG (trademark) 30 | 1.5 | |
| ATTAGEL (trademark) 50 | 15 | |
| TI-PURE (trademark) R-100 | 10 | |
| Balance of water up to 1 liter | | |

EXAMPLE 15

The following emulsion was produced (in g/l):

| | | |
|---|---|---|
| 2,4-DP IOE | 208 | } oily phase |
| 2,4-D TIPA | 325 | |
| Glyphosate IPA | 90 | |
| SOPROMINE (trademark) S30 | 50 | |
| Propylene glycol | 30 | |
| ATLAS (trademark) G3300 | 5 | |
| GERONOL (trademark) 724P | 50 | |
| SAG (trademark) 30 | 1.5 | |
| ATTAGEL (trademark) 50 | 15 | |
| TI-PURE (trademark) R-100 | 10 | |
| Balance of water up to 1 liter | | |

EXAMPLE 16

The following emulsion was produced (in g/l):

| | | |
|---|---|---|
| S,4-D IOE | 191 | } oily phase |
| 2,4-DP IOE | 208 | |
| Glyphosate IPA | 90 | |
| SOPROMINE (trademark) S30 | 50 | |
| Propylene glycol | 30 | |
| ATLAS (trademark) G3300 | 5 | |
| GERONOL (trademark) 724P | 50 | |
| SAG (trademark) 30 | 1.5 | |
| ATTAGEL (trademark) 50 | 15 | |
| TI-PURE (trademark) R-100 | 10 | |
| Balance of water up to 1 liter | | |

EXAMPLE 17

The following emulsion was produced (in g/l):

| | | |
|---|---|---|
| 2,4-D IOE | 352 | } oily phase |
| Glyphosate IPA | 182 | |
| SOPROMINE (trademark) S30 | 100 | |
| Propylene glycol | 30 | |
| ATLAS (trademark) G3300 | 5 | |
| GERONOL (trademark) 724P | 40 | |
| SAG (trademark) 30 | 1.5 | |
| ATTAGEL (trademark) 50 | 15 | |
| TI-PURE (trademark) R-100 | 10 | |
| Balance of water up to 1 liter | | |

EXAMPLE 18

The following emulsion was produced (in g/l):

| | | |
|---|---|---|
| Bromoxynil octanoate | 107 | } oily phase |
| Bromoxynil heptanoate | 106 | |
| TENNECO (trademark) 200 | 80 | |
| Glyphosate IPA | 180 | |
| SOPROMINE (trademark) S30 | 100 | |
| Propylene glycol | 30 | |
| ATLAS (trademark) G3300 | 5 | |
| GERONOL (trademark) 724P | 50 | |
| SAG (trademark) 30 | 1.5 | |
| ATTAGEL (trademark) 50 | 15 | |
| TI-PURE (trademark) R-100 | 10 | |
| Balance of water up to 1 liter | | |

EXAMPLE 19

The following emulsion was produced (in g/l):

| | | |
|---|---|---|
| Bromoxynil octanoate | 71 | } oily phase |
| Bromoxynil heptanoate | 71 | |
| TENNECO (trademark) 200 | 40 | |
| 2,4-D DMA | 337 | |
| Glyphosate IPA | 122 | |
| SOPROMINE (trademark) S30 | 50 | |
| Propylene glycol | 30 | |
| ATLAS (trademark) G3300 | 5 | |
| GERONOL (trademark) 724P | 50 | |
| SAG (trademark) 30 | 1.5 | |
| ATTAGEL (trademark) 50 | 15 | |
| TI-PURE (trademark) R-100 | 10 | |
| Balance of water up to 1 liter | | |

EXAMPLE 20

The following emulsion was produced (in g/l):

| | | |
|---|---|---|
| Bromoxynil octanoate | 71 | } oily phase |
| Bromoxynil heptanoate | 71 | |
| 2,4-D IOE | 235 | |
| TENNECO (trademark) 200 | 40 | |
| Glyphosate IPA | 122 | |
| SOPROMINE (trademark) S30 | 50 | |
| Propylene glycol | 30 | |
| ATLAS (trademark) G3300 | 5 | |
| GERONOL (trademark) 724P | 50 | |
| SAG (trademark) 30 | 1.5 | |
| ATTAGEL (trademark) 50 | 15 | |
| TI-PURE (trademark) R-100 | 10 | |
| Balance of water up to 1 liter | | |

In a similar manner to that described above for EXAMPLES 14-20, other oil-in-water emulsions, EXAMPLES 21-32, can be prepared using other water soluble active ingredients such as those described in the preceding list and oil-soluble active ingredients such as those described in the preceding list.

These examples can include compounds such as:

Acifluorfen sodium: 5-[2-chloro-4-(trifluoromethyl)-phenoxy]-2-nitrobenzoic acid sodium salt;

Dichlorophen sodium: 5,5'-dichloro-2,2'-dihydroxydiphenylmethane;

Glyphosinate ammonium: 4-[hydroxy(methyl)phosphinoyl]-DL-homoalanine ammonium salt;

Imazaquin ammonium: 2-(4-isopropyl-4-methyl-5-oxo-2-imidazolin-2-yl)quinoline-3-carboxylic acid ammonium salt;

Imazaquin: as the acid form in the oil phase;

Imazapyr IPA: 2-(4-isopropyl-4-methyl-5-oxo-2-imidazolin-2-yl)nicotinic acid isopropylammonium salt;

Imazapyr: as the acid form in the oil phase;

Metsulfuron: 2-[3-(4-methoxy-6-methyl-1,3,5-triazin-2-yl)ureidosulfonyl] benzoic acid methyl ester, which optionally may be as a water soluble salt depending upon the pH adjustment by a neutralizing agent;

Pendimethalin: N-(1-ethylpropyl)-2,6-dinitro-3,4-xylidine; or

Chlorsulfuron: 1-(2-chlorophenylsulfonyl)-3-(4-methoxy-6-methyl-1,3,5-triazin-2-yl)urea, which optionally may be as a water soluble salt depending upon the pH adjustment by a neutralizing agent. Examples of these are as follows:

EXAMPLE 21

The following emulsion is produced (in g/l):

| | | |
|---|---|---|
| Bromoxynil octanoate | 142 | } oily phase |
| Bromoxynil heptanoate | 142 | |
| TENNECO (trademark) 200 | 40 | |
| 2,4-D DMA | 415 | |
| Propylene glycol | 30 | |
| ATLAS (trademark) G3300 | 5 | |
| GERONOL (trademark) 724P | 50 | |
| SAG (trademark) 30 | 1.5 | |
| ATTAGEL (trademark) 50 | 15 | |
| METHOCEL (trademark) E50LV | 2 | |
| TI-PURE (trademark) R-100 | 1.2 | |
| Balance of water up to 1 liter | | |

EXAMPLE 22

The following emulsion is prepared (in g/l):

| | | |
|---|---|---|
| 2,4-D IOE | 250 | } oily phase |
| Acifluorfen sodium | 250 | |
| Propylene glycol | 50 | |
| ATLAS (trademark) G3300 | 5 | |
| GERONOL (trademark) 724P | 30 | |
| SAG (trademark) 30 | 1 | |
| CARBODOL (trademark) 910 | 1 | |
| ATTAGEL (trademark) 50 | 15 | |
| TI-PURE (trademark) R-100 | 10 | |
| Balance of water up to 1 liter | | |

EXAMPLE 23

The following emulsion is prepared (in g/l):

| | | |
|---|---|---|
| 2,4-D IOE | 350 | } oily phase |
| Dichlorophen sodium | 200 | |
| Propylene glycol | 50 | |
| GERONOL (trademark) 724P | 40 | |
| ATLAS (trademark) G3300 | 5 | |
| SAG (trademark) 30 | 1 | |
| Carboxymethyl cellulose | 1 | |
| ATTAGEL (trademark) 50 | 15 | |
| TI-PURE (trademark) R-100 | 10 | |
| Balance of water up to 1 liter | | |

EXAMPLE 24

The following emulsion is prepared (in g/l):

| | | |
|---|---|---|
| Bromoxynil octanoate | 150 | } oily phase |
| Glyphosate IPA | 270 | |
| Acifluoren sodium | 150 | |
| SOPROMINE (trademark) S30 | 10 | |
| Propylene glycol | 5 | |
| GERONOL (trademark) 724P | 30 | |
| SAG (trademark) 30 | 0.5 | |
| ATTAGEL (trademark) 50 | 10 | |
| BIOZAN (trademark) | 2 | |
| TI-PURE (trademark) R-100 | 11 | |
| Balance of water up to 1 liter | | |

EXAMPLE 25

The following emulsion is prepared (in g/l):

| | | |
|---|---|---|
| Bromoxynil octanoate | 100 | |
| Bromoxynil heptanoate | 100 | } oily phase |
| SILWET (trademark) L-77 | 100 | |
| TENNECO (trademark) 500/100 | 80 | |
| Glufosinate ammonium | 350 | |
| Propylene glycol | 30 | |
| ATLAS (trademark) G3300 | 5 | |
| GERONOL (trademark) 724P | 40 | |
| SAG (trademark) 30 | 1.5 | |
| ATTAGEL (trademark) 50 | 15 | |
| TI-PURE (trademark) R-100 | 10 | |
| Balance of water up to 1 liter | | |

EXAMPLE 26

The following emulsion is prepared (in g/l):

| | | |
|---|---|---|
| Bromoxynil octanoate | 100 | |
| Bromoxynil heptanoate | 100 | |
| SILWET (trademark) L-77 | 100 | } oily phase |
| TENNECO (trademark) 500/100 | 80 | |
| Metsulfuron | 50 | |
| Dichloromethane | 70 | |
| Glyphosate IPA | 225 | |
| Propylene glycol | 30 | |
| ATLAS (trademark) G3300 | 5 | |
| GERONOL (trademark) 724P | 40 | |
| SAG (trademark) 30 | 1.5 | |
| ATTAGEL (trademark) 50 | 15 | |
| TI-PURE (trademark) R-100 | 10 | |
| Balance of water up to 1 liter | | |

EXAMPLE 27

The following emulsion is prepared (in g/l):

| | | |
|---|---|---|
| 2,4-D IOE | 180 | |
| 2,4-DP IOE | 180 | |
| SILWET (trademark) L-77 | 100 | } oily phase |
| Metsulfuron | 50 | |
| Dichloromethane | 70 | |

-continued

| | | |
|---|---|---|
| Glyphosate IPA | 70 | |
| Propylene glycol | 30 | |
| ATLAS G3300 | 5 | |
| GERONOL (trademark) 724P | 40 | |
| SAG (trademark) 30 | 1.5 | |
| ATTAGEL (trademark) 50 | 15 | |
| TI-PURE (trademark) R-100 | 10 | |
| Balance of water up to 1 liter | | |

EXAMPLE 28

The following emulsion is prepared (in g/l):

| | | |
|---|---|---|
| Pendimethalin | 135 | } oily |
| TENNECO (trademark) 500/100 | 80 | } phase |
| Glyphosate IPA | 135 | |
| SOPROMINE (trademark) S30 | 100 | |
| Propylene glycol | 30 | |
| ATLAS (trademark) G3300 | 5 | |
| GERONOL (trademark) 724P | 40 | |
| SAG (trademark) 30 | 1.5 | |
| ATTAGEL (trademark) 50 | 15 | |
| TI-PURE (trademark) R-100 | 10 | |
| Balance of water up to 1 liter | | |

EXAMPLE 29

The following emulsion is prepared (in g/l):

| | | |
|---|---|---|
| Chlorsulfuron | 25 | } oily |
| SILWET (trademark) L-77 | 100 | } phase |
| Dichloromethane | 100 | |
| Imazaquin ammonium | 225 | |
| Glyphosate IPA | 170 | |
| Propylene glycol | 30 | |
| ATLAS (trademark) G3300 | 5 | |
| GERONOL (trademark) 724P | 40 | |
| SAG (trademark) 30 | 1.5 | |
| ATTAGEL (trademark) 50 | 15 | |
| TI-PURE (trademark) R-100 | 10 | |
| Balance of water up to 1 liter | | |

EXAMPLE 30

The following emulsion is prepared (in g/l):

| | | |
|---|---|---|
| Metsulfuron | 25 | } oily |
| SILWET (trademark) L-77 | 100 | } phase |
| Dichloromethane | 100 | |
| Imazapyr IPA | 175 | |
| Glyphosate IPA | 140 | |
| Propylene glycol | 30 | |
| ATLAS (trademark) G3300 | 5 | |
| GERONOL 724P | 40 | |
| SAG (trademark) 30 | 1.5 | |
| ATTAGEL (trademark) 50 | 15 | |
| TI-PURE (trademark) R-100 | 10 | |
| Balance of water up to 1 liter | | |

EXAMPLE 31

The following emulsion is prepared (in g/l):

| | | |
|---|---|---|
| Pendimethalin | 150 | } oily |
| SILWET (trademark) L-77 | 100 | } phase |
| TENNECO (trademark) 500/100 | 80 | |
| Glufosinate ammonium | 350 | |
| Propylene glycol | 30 | |
| ATLAS (trademark) G3300 | 5 | |
| GERONOL (trademark) 724P | 40 | |

-continued

| | |
|---|---|
| SAG (trademark) 30 | 1.5 |
| ATTAGEL (trademark) 50 | 15 |
| TI-PURE (trademark) R-100 | 10 |
| Balance of water up to 1 liter. | |

EXAMPLE 32

The following emulsion is prepared (in g/l):

| | | |
|---|---|---|
| Imazaquin | 225 | |
| Chlorsulfuron | 25 | |
| SILWET (trademark) L-77 | 100 | } oily |
| TENNECO (trademark) 500/100 | 100 | } phase |
| Dichloromethane | 25 | |
| Glyphosate IPA | 170 | |
| Propylene glycol | 30 | |
| ATLAS (trademark) G3300 | 5 | |
| GERONOL (trademark) 724P | 40 | |
| SAG (trademark) 30 | 1.5 | |
| ATTAGEL (trademark) 50 | 15 | |
| TI-PURE (trademark) R-100 | 10 | |
| Balance of water up to 1 liter. | | |

It is to be understood that although the invention has been described with specific references to particular embodiments thereof, it is not to be so limited, since changes and alterations therein may be made which are within the full intended scope of this invention as defined by the appended claims.

What we claim is:

1. A stabilized oil-in-water (O/W) macroemulsion, comprising in grams/liter:

| | | | |
|---|---|---|---|
| a. | an oil phase lipophilic pesticidal substance, optionally dissolved in an organic solvent, wherein the average dispersed oil droplet particle size is between about 1 and about 8 microns; | 25 to 800 | } oily phase |
| b. | an organic solvent; | 0 to 350 | |
| c. | a hydrophobic surface-active emulsifying agent; | 0 to 100 | |
| d. | a hydrophilic surface-active emulsifying agent; | 20 to 60 | |
| e. | a water phase compatible water soluble pesticidal substance; | 20 to 600 | |
| f. | a titanium dioxide-based emulsion dispersing or stabilizing agent, being a fine powder with an average particle size between about 0.1 and about 1 microns, to effectively maintain or improve the stability of the emulsion; and | 1 to 100 | |
| g. | water; | balance to 1,000. | |

2. The stabilized O/W emulsion of claim 1, wherein the lipophilic pesticidal substance has a melting point below about 100° C.

3. The stabilized O/W emulsion of claim 2 wherein the lipophilic pesticidal substance has a melting point situated within the range of temperature variation to which the said lipophilic pesticidal substance is subjected, during storage or preparation of the emulsion.

4. The stabilized O/W emulsion of claim 3, wherein the range of temperature variation during storage or preparation of the emulsion is between about −20° C. and about +60° C.

5. The stabilized O/W emulsion of claim 1, wherein the oil droplet particle size distribution is between about 1 and about 15 microns.

6. The stabilized O/W emulsion of claim 5, wherein the titanium dioxide powder:
   a. is in a proportion of about 10 g/l to about 30 g/l; and
   b. has an average particle size from about 2% to about 50% of the average oil phase droplet particle size.

7. The stabilized O/W emulsion of claim 6, wherein the average particle size of the titanium dioxide powder is in the range of about 0.2 to about 0.3 microns.

8. The stabilized O/W emulsion of claims 1 or 7, wherein the titanium dioxide powder has a substantially hydrophilic surface, which is not easily wetted by either oil or water phase.

9. The stabilized O/W emulsion of claim 6, wherein:
   a. the oil phase lipophilic pesticidal substance is phosalone, oxadiazon, aclonifen, linuron, bifenox, alachlor, ethoprofos, bromoxynil octanoate or heptanoate, ethion, 2,4-D isooctyl ester, 2,4-DP isooctyl ester, metsulfuron, pendimethalin, or chlorsulfuron or mixtures thereof; and
   b. the water phase, water soluble pesticidal substance is a glyphosate salt, a 2,4-D salt, an acifluorfen salt, a dichlorphen salt, glufosinate salt, an imazaquin salt, or an imazapyr salt or mixtures thereof.

10. The stabilized O/W emulsion of claim 9, wherein the lipophilic pesticidal substance is: a mixture of bromoxynil octanoate and heptanoate, containing from about 100 to about 600 g/l of the mixed esters, based upon bromoxynil phenol; a mixture of aclonifen and linuron; or 2,4-D isooctyl ester or 2,4-DP isooctyl ester or a mixture thereof.

11. The stabilized O/W emulsion of claim 9, wherein the water soluble pesticidal substance is glyphosate isopropylamine salt, 2,4-D triisopropylamine salt, or 2,4-D dimethylamine salt, or mixtures thereof.

12. The stabilized O/W emulsion of claim 1 which further comprises other additives selected from the group consisting of antifoam agents, antifreeze agents, thickening agents, wetting agents, and penetrating agents.

13. The stabilized O/W emulsion of claim 1, which further comprises a suspended solid pesticidal substance obtained by mixing and milling the emulsion and the solid to provide a stable suspoemulsion.

14. The stabilized O/W suspoemulsion of claim 13, wherein the suspoemulsion is diluted with water to provide a diluted, stable O/W suspoemulsion pesticidal composition.

15. The stabilized O/W emulsion of claim 1, wherein the emulsion is diluted with water to provide a diluted, stable O/W emulsion pesticidal composition.

* * * * *